(12) United States Patent
Lee

(10) Patent No.: US 6,206,852 B1
(45) Date of Patent: Mar. 27, 2001

(54) BALLOON CATHETER HAVING A SMALL PROFILE CATHETER

(75) Inventor: Jeong Soo Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/464,365

(22) Filed: Dec. 15, 1999

(51) Int. Cl.$^7$ .................................................. A61M 29/00
(52) U.S. Cl. ........................................................ 604/96.01
(58) Field of Search ................................ 604/96.01, 264, 604/22, 101.01–101.05; 606/167, 168, 169, 170, 171, 172, 173, 174, 185, 184

(56) References Cited

U.S. PATENT DOCUMENTS

| | | | |
|---|---|---|---|
| 958,854 | * 5/1910 | Bunn | 606/192 |
| 3,173,418 | 3/1965 | Baran . | |
| 3,645,268 | * 2/1972 | Capote | 128/347 |
| 3,734,100 | 5/1973 | Walker et al. . | |
| 3,890,976 | 6/1975 | Bazell et al. . | |
| 3,971,385 | 7/1976 | Corbett . | |
| 4,489,722 | 12/1984 | Ferraro et al. . | |
| 4,588,399 | 5/1986 | Nebergall et al. . | |
| 4,617,019 | 10/1986 | Fecht et al. . | |
| 4,622,968 | * 11/1986 | Persson | 604/165 |
| 4,708,147 | * 11/1987 | Haaga | 128/753 |
| 4,850,960 | 7/1989 | Grayzel . | |
| 4,894,051 | 1/1990 | Shiber . | |
| 4,950,257 | * 8/1990 | Hibbs et al. | 604/265 |
| 4,990,138 | 2/1991 | Bacich et al. . | |
| 5,057,083 | 10/1991 | Gellman . | |
| 5,282,785 | 2/1994 | Shapland et al. . | |
| 5,295,969 | * 3/1994 | Fischell et al. | 604/168 |
| 5,395,330 | 3/1995 | Marcadis et al. . | |
| 5,472,419 | 12/1995 | Bacich . | |
| 5,484,416 | 1/1996 | Gittings . | |
| 5,586,991 | * 12/1996 | Yoon | 606/185 |
| 5,637,086 | * 6/1997 | Ferguson et al. | 604/96 |
| 5,653,690 | 8/1997 | Booth et al. . | |
| 5,662,607 | 9/1997 | Booth et al. . | |
| 5,662,674 | * 9/1997 | Debbas | 606/192 |
| 5,746,709 | 5/1998 | Rom et al. . | |
| 5,797,943 | * 8/1998 | Danks et al. | 606/167 |
| 5,807,329 | 9/1998 | Gelman . | |
| 5,830,227 | 11/1998 | Fischell et al. . | |
| 6,022,367 | * 2/2000 | Sherts | 606/184 |
| 6,030,403 | * 2/2000 | Long et al. | 606/185 |

* cited by examiner

*Primary Examiner*—Manuel Mendez
(74) *Attorney, Agent, or Firm*—Heller Ehrman White & McAuliffe LLP

(57) ABSTRACT

This invention is directed at an intravascular balloon catheter. The most important aspect of this invention is the catheter tip which is small, soft and truncated. The tip member has a proximal end and a distal end. The proximal end is secured to the distal end of the inner tubular member of the catheter shaft. The distal end has proximal and distal leading edges which reduce the overall profile of the catheter. Moreover, the catheter tip is formed from pliant materials so that trauma to the blood vessel walls can be minimized.

14 Claims, 3 Drawing Sheets

BALLOON CATHETER HAVING A SMALL PROFILE CATHETER

BACKGROUND

This invention generally relates to intravascular catheters used for stent delivery and percutaneous transluminal coronary angioplasty (PTCA).

PTCA is a widely used procedure for the treatment of coronary heart disease. In this procedure, a balloon on the catheter is inflated within the stenotic region of the patient's artery to open up the arterial passageway and thereby increase the blood flow through the artery.

Typically, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent to the ostium of the desired coronary artery; and the distal tip of the guiding catheter is then maneuvered into the ostium. A balloon dilation catheter may then be advanced through the guiding catheter into the patient's coronary artery until the balloon on the catheter is disposed within the stenotic region of the patient's artery. The balloon is inflated to open up the arterial passageway. Generally, the inflated diameter of the balloon is approximately the same diameter as the native diameter of the body lumen being dilated so as to complete the dilation but not over expand the artery wall. After the balloon is finally deflated, blood flow resumes through the dilated artery and the dilation catheter can be removed.

A continual effort has been made in the development of intravascular catheters, to reduce the transverse dimensions or profiles of such catheters, particularly at the catheter tip. A catheter having a small or reduced profile generally has a greater ability to cross lesions and tight vasculatures. Despite much technical progress in this area, the need for intravascular catheters having greater reduced profiles at the catheter tip remains. The present invention satisfies these needs.

SUMMARY

The present invention is an intravascular balloon catheter having a small profile distal tip. In one embodiment, the distal tip generally includes a forward face with a proximal edge and a distal edge on opposite sides of the catheter shaft and a face which tapers in a distal direction from the proximal edge to the distal edge. Because the tip member is tapered from the proximal edge to the distal edge, the shape of the distal tip is similar to that of a truncated cylinder which provides the distal edge of the tip member with a low profile. The small profile and chisel-like shape of the truncated distal tip improves the overall ability of this catheter to cross any stenosis. Once the distal edge is eased through a stenosed region, sections of the catheter proximal thereto can be readily advanced across the stenosis. The truncated distal tip defines an elliptical port in the distal end thereof. The elliptical port facilitates backloading of a guidewire into the guidewire lumen of the catheter shaft, in which the proximal end of the guidewire is introduced into the distal port of the catheter, by providing a larger opening than the cylindrical port of a prior art distal tip.

The distal tip may be formed as a single unit with the catheter shaft, or alternatively, as a separate member which is secured to a distal end of the catheter shaft. The distal tip is preferably formed of a soft material, to thus avoid causing trauma and tissue damage as it is advanced through the blood vessels.

In another embodiment, the truncated distal tip further includes a first side and a second side on opposite sides of the catheter shaft longitudinal axis, the first side and the second side each tapering distally toward a center of the catheter shaft from a larger outer diameter to a smaller outer diameter, to thus form a wedge-like structure.

Another embodiment of the invention generally comprises a distal tip with a proximal end, and a distal end having an outer diameter along a first plane which is not less than an outer diameter of the proximal end of the distal tip, and with a first side and a second side on opposite sides of the catheter shaft longitudinal axis, the first side and the second side each tapering distally along a second plane toward a center of the catheter shaft from a larger outer diameter to a smaller outer diameter, to thus form a structure typical of some flat head screwdrivers but with a lumen therein.

Unlike the blunt cylindrical tip members of the catheters currently available, the profile of the catheter of the invention is much lower and this improves the ability of the catheter to cross narrowed stenosed regions and to be advanced within narrow vessels. These and other advantages will become more apparent from the following detailed description and accompanying exemplary drawings.

DETAILED DESCRIPTION

Figure 1:
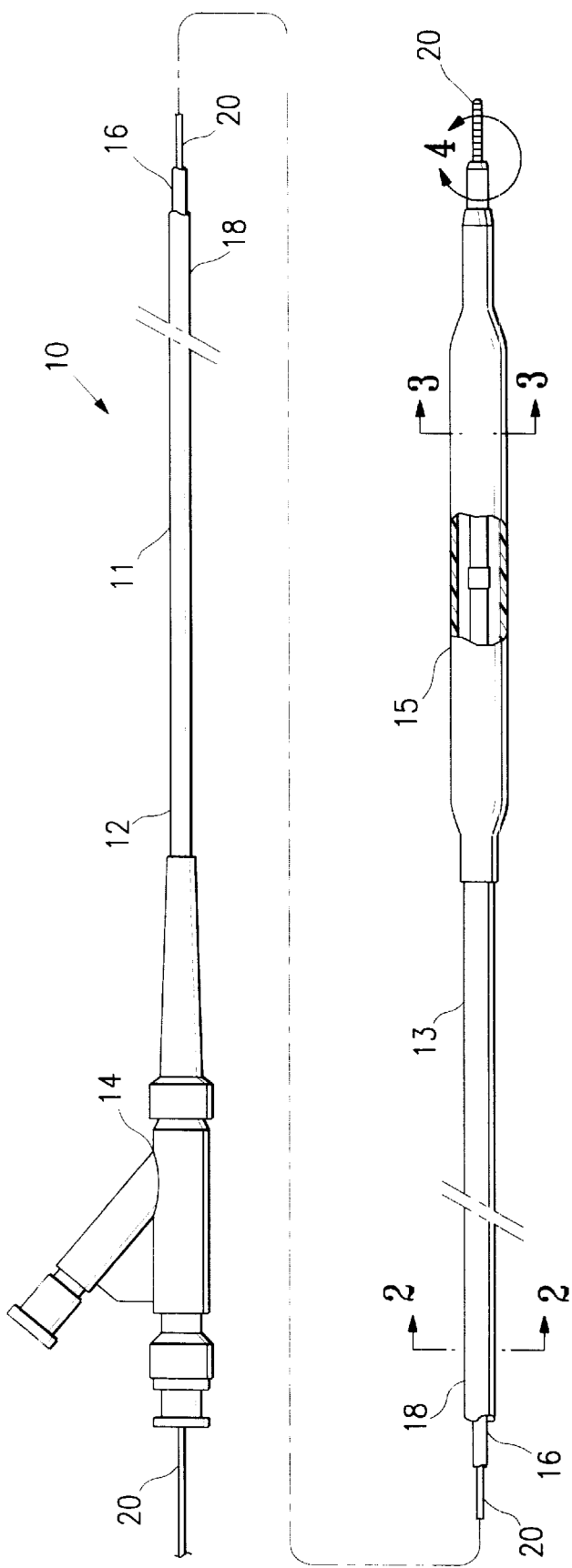
FIG. 1 is an elevational view, partially in section, of a balloon catheter with guidewire in the inner lumen of the catheter.
Figure 3:
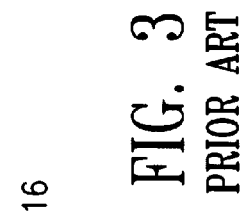
FIG. 3 is a transverse cross-sectional view of the catheter assembly shown in FIG. 1 taken along the lines 3—3.
Figure 2:
FIG. 2 is a transverse cross-sectional view of the catheter assembly shown in FIG. 1 taken along the line 2—2.

FIG. 1 illustrates a prior art intravascular balloon catheter 10 having an elongated catheter shaft 11 having a proximal section 12, a distal section 13, an adapter 14 secured to a proximal end of the shaft, and an inflatable balloon 15 on the distal shaft section. In the embodiment illustrated in FIG. 1, the catheter shaft comprises an inner tubular member 16 defining a guidewire lumen 17, within an outer tubular member 18 that is disposed about the inner tubular member and defines therewith inflation lumen 19. FIG. 2 illustrates the transverse cross sectional view of the catheter taken along line 2—2, and FIG. 3 illustrates the transverse cross sectional view of the catheter taken along line 3—3. Guidewire 20 is disposed within guidewire lumen 17.

Figure 4:
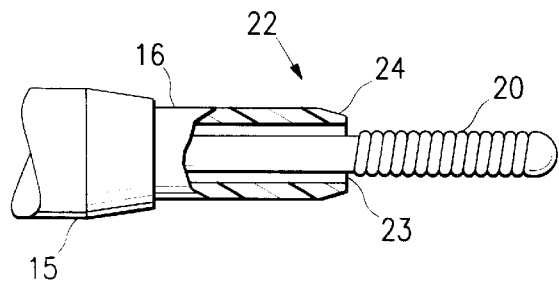
FIG. 4 is an enlarged longitudinal, partial in section, view of the catheter shown in FIG. 1 taken in circle 4, illustrating a prior art catheter distal tip.
Figure 5:
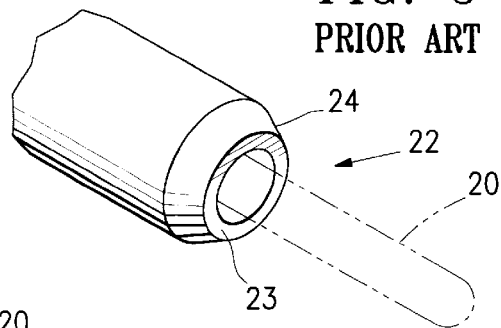
FIG. 5 is a perspective view of the catheter distal tip shown in FIG. 1 with the guidewire shown in phantom.

In the embodiment illustrated in FIG. 1, the catheter has a conventional, prior art tapered distal tip 22, as best illustrated in FIG. 4 showing an enlarged view of the distal tip of FIG. 1, taken within circle 4. FIG. 5 illustrates a perspective view of the distal tip shown in FIG. 4. The prior art tapered distal tip 22 shown in FIGS. 4 and 5 is cylindrical in shape, with a blunt, flat tip 23 and tapered sides 24.

Figure 6:
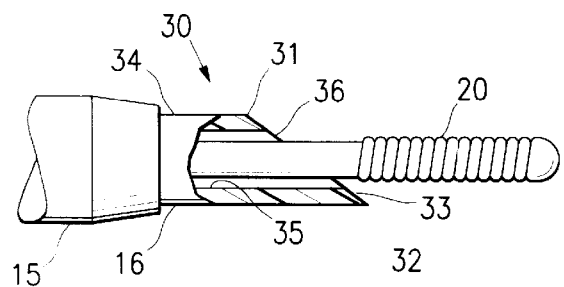
FIG. 6 is an enlarged longitudinal, partial in section, view of a catheter distal tip which embodies features of this invention, having a truncated tip member.
Figure 7:
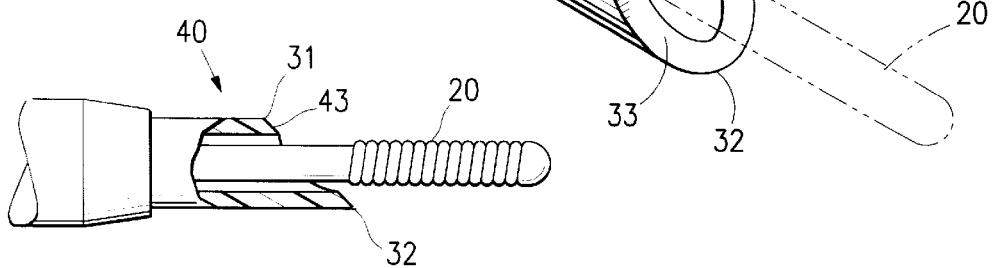
FIG. 7 is a perspective view of the catheter tip illustrated in FIG. 6 with the guidewire shown in phantom.

FIGS. 6 and 7 illustrates an embodiment of the distal tip of the invention, generally comprising a truncated distal tip 30. It should be understood that the distal tip shown in FIGS. 6 and 7, and the additional embodiments discussed below, could be used on catheter 10 shown in FIG. 1 in place of the conventional distal tip 22 illustrated in FIG. 1, so that the distal tip 30 is on the distal end of inner tubular member 16. FIG. 6 is a longitudinal, partial in section view of the truncated and tapered catheter tip 30, and FIG. 7 is a perspective view of the truncated catheter tip 30. Distal tip 30 has a proximal edge 31, a distal edge 32 on an opposite side of the catheter shaft, and a face 33 which tapers in a distal direction from the proximal edge 31 to the distal edge 32. As illustrated in FIGS. 6 and 7, the proximal edge 31 and distal edge 32 of the distal tip 30 are substantially longitudinally aligned with an outer surface 34 of the inner tubular member. The phrase "substantially longitudinally aligned" should be understood to mean that the inner tubular member has an outer diameter equal to or only slightly different from the outer diameter at the proximal and distal edges 31/32 of the distal tip 30. The outer surface 34 of the inner tubular member 16 is axially aligned with the longitudinal axis of the inner tubular member. Distal tip 30 defines lumen 35 therein, in fluid communication with guidewire lumen 17 of the inner tubular member 16. Distal tip 30 defines an elliptical port 36 in the distal end thereof.

Face 33 of distal tip 30 is shown in FIG. 6 generally tapering at an angle of about 45 degrees. However, face 33 may taper at a variety of suitable angles. An angle of about 30 to about 45 degrees is generally preferred, for ease of manufacturing. In the presently preferred embodiment illustrated in FIGS. 6 and 7, the inner tubular member distal tip 30 has an inner diameter (i.e., the diameter of lumen 35) which is equal to or not less than an inner diameter of the inner tubular member 16 (i.e., the diameter of lumen 17) at a location proximal to the distal tip 30. The inner diameter of the distal tip 30 is typically about 0.36 mm to about 0.48 mm preferably about 0.40 mm to about 0.45 mm. In the embodiment illustrated in FIGS. 6 and 7, distal tip 30 has an outer diameter measured from the proximal edge 31 to the distal edge 32 which is not less than an outer diameter of the inner tubular member 16 at a location proximal to the distal tip. The inner tubular member distal tip 30 has an outer diameter measured from the proximal edge 31 to the distal edge 32 which is typically about 0.45 mm to about 1.0, preferably about 0.45 to about 0.5, and a length which is typically about 0.5 mm to about 1.5 mm, preferably about 0.5 mm to about 1.0 mm.

Figure 8:
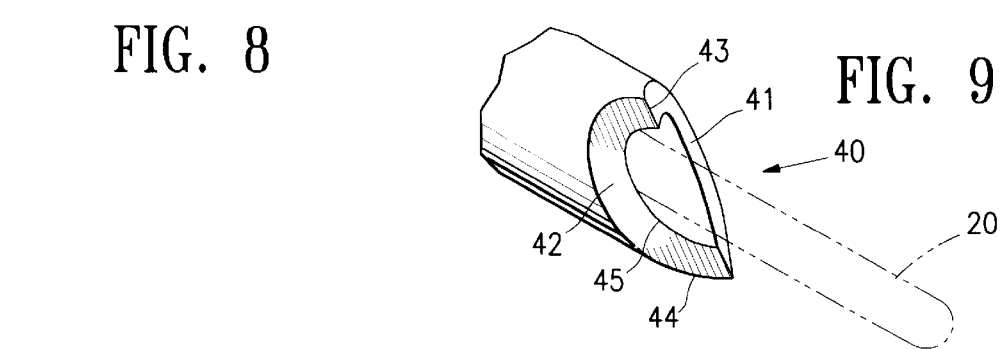
FIG. 8 is an enlarged longitudinal, partial in section, view of a truncated distal tip embodying features of the invention, having first and second tapered sides.
Figure 9:
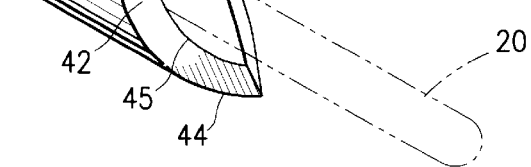
FIG. 9 is a perspective view of the tip shown in FIG. 8 with the guidewire shown in phantom.

FIGS. 8 and 9 illustrate another embodiment of the invention comprising distal tip 40. Distal tip 40 generally comprises the distal tip 30 shown in FIGS. 6 and 7, further including a first side 41, a second side 42 on an opposite side of the inner tubular member 16 longitudinal axis, the first side 41 and second side 42 each tapering distally toward a center 43 of the inner tubular member 16 from a larger outer diameter edge 44 to a smaller outer diameter edge 45. FIG. 9 illustrates a perspective view of distal tip 40 shown in FIG. 8.

Figure 10:
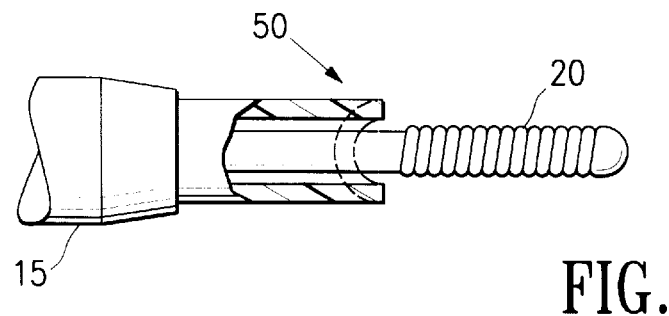
FIG. 10 is an enlarged longitudinal, partial in section, view of a catheter tip which embodies features of the invention, having first and second tapered sides forming a flat head screwdriver shaped distal tip.
Figure 11:
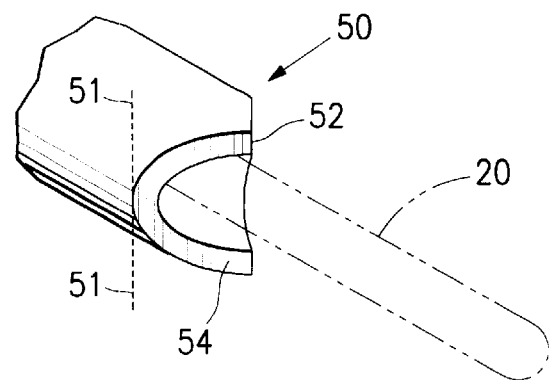
FIG. 11 is a perspective view of the distal tip shown in FIG. 10 with the guidewire shown in phantom.
Figure 12:
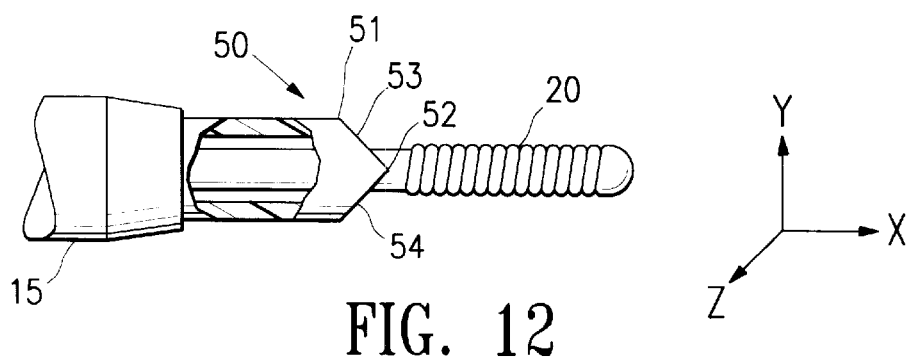
FIG. 12 is a plan view of the distal tip shown in FIG. 10.

FIGS. 10–12 illustrate another embodiment of the invention, comprising distal tip 50 generally having a flat head screwdriver shape. Distal tip 50 has a proximal end 51, and a distal end 52 having an outer diameter along a first plane Z which is not less than an outer diameter of the proximal end 51 of the distal tip, and with a first side 53 and a second side 54 on opposite sides of the inner tubular member longitudinal axis, the first side 53 and the second side 54 each tapering distally in a second plane X inwardly toward a center of the inner tubular member from a larger outer diameter to a smaller outer diameter. The distal end of the first side 53 of the distal tip adjoins, or may be adjacent to, the distal end of the second side 54 of the distal tip to form the distal end 52 of the distal tip 50. FIG. 10 is a longitudinal, partially in section, view of the distal tip 50, FIG. 11 is a perspective view of the distal tip 50 shown in FIG. 10, and FIG. 12 is a plan view of the distal tip 50.

Figure 13:
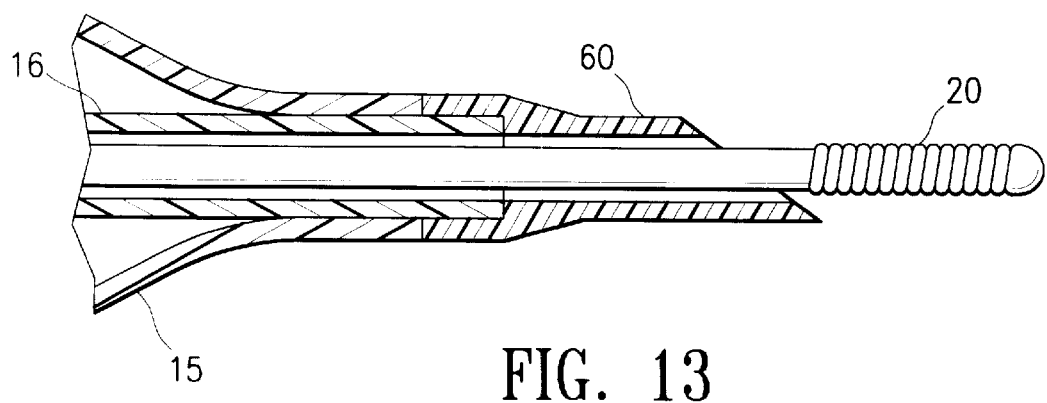
FIG. 13 is an enlarged longitudinal, partial in section, view of a catheter tip member which embodies features of the invention, with a separate tip member secured to the catheter shaft.

The distal tip of the invention may be formed as a single unit with the inner tubular member 16, or alternatively, as illustrated in FIG. 13, distal tip may be a separate unit 60 secured to the distal end of the inner tubular member 16. FIG. 13 is an enlarged longitudinal partial in section view of distal tip 60, which may be secured to inner tubular member 16 using conventional means such as adhesive or fusion bonding. The figure also illustrates how the inner lumen of the tip member is in fluid communication with the inner lumen of the catheter shaft. The balloon 15 distal shaft section may be secured to either one or both of the inner member 16 and the distal tip 30/40/50/60.

The wall thickness of the distal tip of the invention is typically about 0.03 mm to about 0.04 mm. The small non-cylindrical tip member is typically produced from polymeric materials such as polyamide copolymers such as PEBAX (a polyether block amide), polyurethanes, and polyolefins, and with a Shore Durometer hardness which is preferably about 45 D to about 65 D. Forming the tip member from the above materials makes for a soft tip member that transmits less trauma as the catheter is advanced through the body.

While the invention has been discussed in terms of certain preferred embodiments, it should be understood that various modifications may be made without departing from the scope thereof. Moreover, although certain individual features of one embodiment of the invention may be discussed herein or shown in the drawings of the one embodiment and not in other embodiments, it should be apparent that individual features of one embodiment may be combined with one or more features of another embodiment.

What is claimed:

1. A balloon catheter, comprising:
   an elongated shaft having a proximal end, a distal end, and proximal and distal sections disposed therebetween;
   an inflatable member disposed on the distal shaft section and having a proximal end, a distal end at a location proximal to the shaft distal end, and an interior chamber;
   an inflation lumen extending within at least a portion of the elongated shaft to a location proximal to the shaft distal end and in fluid communication with the inflatable member interior chamber;

a guidewire receiving lumen defined, at least in part, by a tubular member sealingly secured to the inflatable member distal end, and extending through at least the distal section of the elongated shaft to the shaft distal end, and having a distal tip with proximal and distal edges on opposite sides of the distal tip and a face tapering in a distal direction from the proximal edge to the distal edge.

2. The catheter of claim 1 wherein the proximal edge and the distal edge of the distal tip are substantially longitudinally aligned with an outer surface of the inner tubular member, the outer surface of the inner tubular member being axially aligned with the longitudinal axis of the inner tubular member.

3. The catheter of claim 1 wherein the face of the distal tip tapers at an angle of about 30 to about 45 degrees.

4. The catheter of claim 1 wherein the face of the distal tip tapers at an angle of about 45 degrees.

5. The catheter of claim 1 wherein the inner diameter of the inner tubular member distal tip is about 0.36 mm to about 0.48 mm.

6. The catheter of claim 1 wherein the inner tubular member distal tip has an inner diameter which is not less than an inner diameter of the inner tubular member at a location proximal to the distal tip.

7. The catheter of claim 1 wherein the outer diameter of the inner tubular member distal tip measured from the proximal edge to the distal edge of the distal tip is about 0.45 mm to about 1.0 mm.

8. The catheter of claim 1 wherein the inner tubular member distal tip has an outer diameter measured from the proximal edge to the distal edge of the distal tip which is not less than an outer diameter of the inner tubular member at a location proximal to the distal tip.

9. The catheter of claim 1 wherein the distal tip comprises a tip member having a proximal end secured to the distal end of the inner tubular member, and a lumen in fluid communication with the inner tubular member lumen.

10. The dilation catheter of claim 1 wherein a wall thickness of the distal tip of the inner tubular member is about 0.03 to 0.04 mm.

11. The dilation catheter of claim 1 wherein the tip member is formed of a polymeric material selected from the group consisting of a polyamide copolymer, polyurethane, and polyolefin.

12. The catheter of claim 1 wherein the distal tip includes a first side and a second side on opposite sides of the inner tubular member longitudinal axis, the first side and the second side each tapering distally toward a center of the inner tubular member from a larger outer diameter to a smaller outer diameter.

13. A balloon catheter, comprising:

an elongated shaft having a proximal end, a distal end, and proximal and distal sections disposed therebetween;

an inflatable member disposed on the distal shaft section and having a proximal end, a distal end at a location proximal to the shaft distal end, and an interior chamber;

an inflation lumen extending within at least a portion of the elongated shaft to a location proximal to the shaft distal end and in fluid communication with the inflatable member interior chamber;

a guidewire receiving lumen defined, at least in part, by a tubular member sealingly secured to the inflatable member distal end, and extending through at least the distal section of the elongated shaft to the shaft distal end, and having a distal tip with a proximal end, and a distal end having an outer diameter along a first plane not less than an outer diameter of the proximal end of the distal tip, and with a first side and a second side on opposite sides of the inner tubular member longitudinal axis, the first side and the second side each distally tapering in a second plane perpendicular to the first plane inwardly toward a center of the inner tubular member from a larger outer diameter to a smaller outer diameter.

14. The catheter of claim 13 wherein the distal end of the first side of the distal tip adjoins the distal end of the second side of the distal tip to form the distal end of the distal tip.

* * * * *